United States Patent
Patil et al.

(10) Patent No.: US 10,301,330 B2
(45) Date of Patent: May 28, 2019

(54) N, C-CHELATE FOUR-COORDINATE ORGANOBORONS WITH FULL COLOURTUNABILITY

(71) Applicant: COUNCIL OF SCIENTIFIC & INDUSTRIAL RESEARCH, New Delhi (IN)

(72) Inventors: Nitin Tukaram Patil, Pune (IN); Aslam Chandbhai Shaikh, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/738,677

(22) PCT Filed: Jun. 22, 2016

(86) PCT No.: PCT/IN2016/050193
§ 371 (c)(1),
(2) Date: Dec. 21, 2017

(87) PCT Pub. No.: WO2016/207910
PCT Pub. Date: Dec. 29, 2016

(65) Prior Publication Data
US 2018/0346490 A1 Dec. 6, 2018

(30) Foreign Application Priority Data
Jun. 22, 2015 (IN) .......................... 1844/DEL/2015

(51) Int. Cl.
*C07F 5/02* (2006.01)
*H01L 51/00* (2006.01)
*C09K 11/06* (2006.01)
*H01L 51/50* (2006.01)

(52) U.S. Cl.
CPC .............. *C07F 5/027* (2013.01); *C09K 11/06* (2013.01); *H01L 51/008* (2013.01); *C09K 2211/1014* (2013.01); *C09K 2211/1022* (2013.01); *C09K 2211/1029* (2013.01); *C09K 2211/1092* (2013.01); *H01L 51/5012* (2013.01)

(58) Field of Classification Search
CPC ....................................................... C07F 5/02
USPC ............................................ 546/13; 313/498
See application file for complete search history.

(56) References Cited
U.S. PATENT DOCUMENTS
2012/0264044 A1  10/2012  Ikeda et al.

FOREIGN PATENT DOCUMENTS
WO  2011/0099331  8/2011

OTHER PUBLICATIONS

Bonardi, L., et al., "Fine-Tuning of Yellow or Red Photo- and Electroluminescence of Functional Difluoro-boradiazaindacene Films", Advanced Functional Materials 2008,18:401-413.
Zhao, Z, et al., "Aggregation-Induced Emission and Efficient Solid-State Fluorescence from Tetraphenylethene-Based N, C-Celate Four-Coordinate Organoborons", Chem. Eur. J. 2013, 19:11512-11517.
Ishida, N., et al., "Synthesis of Pyridine-Borane Complexes via Electrophilic Aromatic Borylation", J. Org. Chem. 2010, 75:8709-8712.
Liu, Q., et al., "From Blue to Red: Syntheses, Structures, Electronic, and Electroluminescent Properties of Tunable Luminescent N, N Chelate Boron Complexes", Advanced Functional Materials 2005, 15:143-154.
Rao, Ying-Li and Suning Wang, "Four-Coordinate Organoboron Compounds with a Π-Conjugated Chelate Ligand for Optoelectronic Applications", American Chemical Society 2011, 50:12263-12274.
Patil, Nitin T. and Vivek S. Raut, "Cooperative Catalysis with Metal and Secondary Amine: Synthesis of 2-Substituted Quinolines via Addition/Cycloisomierization Cascade", J. Org. Chem. 2010, 75:6961-6964.
Rao, Ying-Li, et al., "Photochromic four-coordinate N,C-chelate boron compounds", Coordination Chemistry Reviews 2012, 256:759-770.
Baik, C., et al., "Enhancing the Photochemical Stability of N,C-Chelate Boryl Compounds: C—C Bond Formation versus C=C Bond cis,trans-Isomerization", J. Am. Chem. Soc. 2009, 131(40):14549-14559.
Amarne, Hazem, et al., "Steric and Electronic Influence on Photochromic Switching of N,C-Chelate Four-Coordinate Organoboron Compounds", Chem. Eur. J. 2010, 16:4750-4761.

*Primary Examiner* — Charanjit Aulakh
(74) *Attorney, Agent, or Firm* — Melissa M. Hayworth; E. Joseph Gess

(57) ABSTRACT

The present invention relates to novel full-color tunable light emitter based on N,C-chelate four-coordinate organoborons having excellent Quantum yield, stokes shift and solvate chromism of Formula (I);

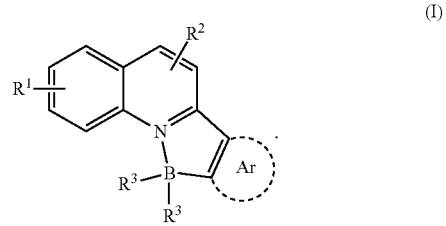

(I)

6 Claims, 2 Drawing Sheets

Fig: 1a

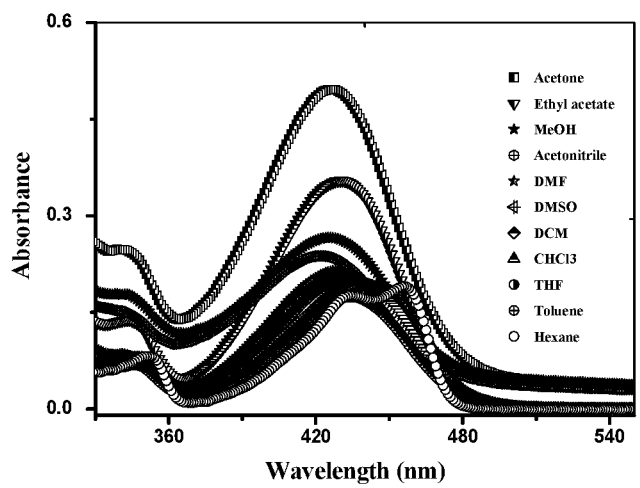
Fig: 2a
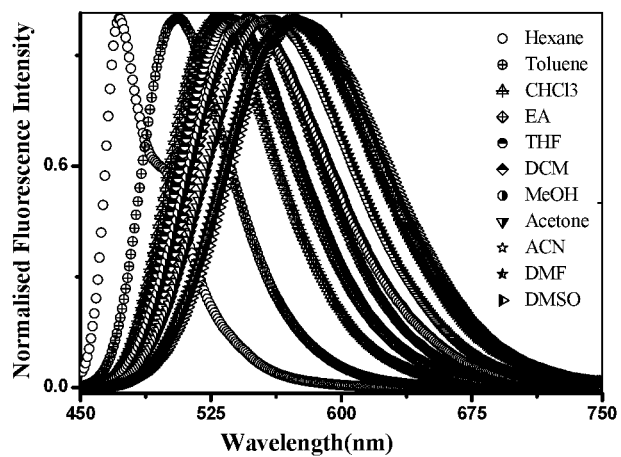
Fig: 2b

N, C-CHELATE FOUR-COORDINATE ORGANOBORONS WITH FULL COLOURTUNABILITY

RELATED APPLICATIONS

The present application is a 371 National Stage of PCT/IN2016/050193 filed on 22 Jun. 2016, which claims the benefit of Indian Provisional Patent Application No. 1844/DEL/2015 filed on 22 Jun. 2015.

FIELD OF THE INVENTION

The present invention relates to novel full-color tunable light emitter based on N,C-chelate four-coordinate organoborons having excellent Quantum yield, stokes shift and solvate chromism of Formula (I);

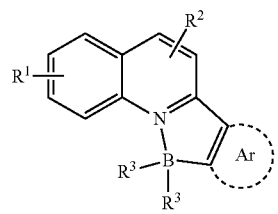

Formula (I)

BACKGROUND AND PRIOR ART

Organic optoelectronic devices are becoming widely desirable due to various reasons such as the organic devices are cost effective, the inherent properties of the organic material such as flexibility, fluorescent properties, color tunability using functionalized molecules make them suitable for particular applications.

Designing of luminescent organic material plays a pivotal role in development of optoelectronic devices with improved energy consumption. Research is more focused on providing solid light emitters for their practical applications in optoelectronic devices, such as organic light-emitting diodes. The solid state fluorescent material known in the art are heavily relied on mere functionalization of existing fluorophores. However, considering the demand of solid light emitters in material science and biology, there is an urgent need for the identification of novel core structures, with full colour-tunability, capable of emitting light in the aggregation state.

Organoborons have attracted considerable attention in the scientific fraternity due to their unique electronic structure and interesting optical property derived from the intrinsic $p_{\pi}$-$p^*$ conjugation between the vacant $p_x$-orbital of the boron atom and the $\Pi^*$ orbital of the p-conjugated framework.

The most potential examples of fluorescent organoboron compounds are borondipyrromethene (BODIPY) dyes and its analogues which are only emissive in dilute solutions and their fluorescence is quenched severely in the aggregate state [L. Bonardi, H. Kanaan, F. Camerel, P. Jolinat, P. Retailleau, R. Ziessel, Adv. Funct. Mater. 2008, 18, 401]. Hence, a more robust highly emissive solid organoborons are needed.

PCT application WO2011099331, discloses a novel boron-containing compound which is useful as a light-emitting material for organic EL elements or N-type semiconductors; a boron-containing polymer obtained using the compound; and a process for the preparation of the boron-containing compound, which enables low-cost production of the boron-containing compound and the boron-containing polymer. A light-emitting material which contains a boron-containing compound that has a boron atom and a double bond and that has a specific structure. A luminescent material comprising a boron-containing compound having a boron atom and a double bond, the boron-containing compound represented by the following formula (1);

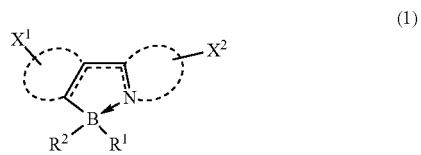

(1)

Article titled "Aggregation-induced emission and efficient solid-state fluorescence from tetraphenylethene-based N,C-chelate four-coordinate organoborons" by Zujin Zhao et al. published in Chemistry European Journal, 2013, 19, 11512-11517 reports boron compounds containing the TPE moiety and N,C-chelate of formula 2 and to the synthesis thereof. Here quantum yield of chelate compounds are 0.40, 0.94 and 0.019.

Article titled "Synthesis of pyridine-borane complexes via electrophilic aromatic borylation" by Naoki Ishida et al. published in Journal of Organic Chemistry, 2010, 75, 8709-8712 reports synthesis of Pyridine-borane complexes from 2-arylpyridines through an electrophilic aromatic borylation reaction with $BBr_3$.

Article titled "From blue to red: syntheses, structures, electronic and electroluminescent properties of tunable luminescent N,N chelate boron complexes" by Q. D. Liu et al. published in *Advances Functional Materials,* 2005, 15, 1, pp 143-154 reports A comprehensive study of a series four-coordinate boron compounds with the general formula of $BPh_2(N,N)$, where N,N are bidentate chelate ligands containing both neutral and negatively charged nitrogen donor atoms has been conducted. The structures of the boron complexes were examined via single-crystal X-ray diffraction.

Article titled "Four-coordinate organoboron compounds with a π-conjugated chelate ligand for optoelectronic applications" by Ying-Li Rao et al. published in *Inorganic Chemistry,* 2011, 50 (24), pp 12263-12274 reports Four-coordinate organoboron compounds that possess a conjugated chelate ligand have found important applications in advanced materials including emitters and electron-transport materials for organic light-emitting diodes, photochromic materials, and sensing and imaging materials. The recent advances in optoelectronic applications of four-coordinate organoboron compounds are presented in this article.

Article titled "Cooperative catalysis with metal and secondary amine: synthesis of 2-substituted quinolines via addition/cycloisomerization cascade" by Nitin T. Patil et al. published in *Journal of Organic Chemistry,* 2010, 75 (20), pp 6961-6964 reports a cooperative catalytic system, consisting of CuI and pyrrolidine, has been developed for an efficient synthesis of 2-substituted quinolines. A combination of both the catalysts is necessary; the use of either catalyst alone does not give the product.

Article titled "Photochromic four-coordinate N,C-chelate boron compounds" by Ying-Li Rao et al. published in Coordination Chemistry Reviews, 2012, 256, 5-8, pp 759-770 reports four-coordinate organoboron compounds with a N,C-chelate backbone have been found recently to display an unusual photoisomerization phenomenon with a distinct change of color.

Article titled "Enhancing the photochemical stability of N,C-chelate boryl compounds: C—C bond formation versus C═C bond cis, trans-isomerization." by Chul Baik et al. published in Journal of American Chemical Society, 2009, 131, 14549-14559 reports N,C-Chelate boron compounds such as B(ppy)Mes$_2$ (ppy=2-phenylpyridyl, Mes=mesityl) have been recently shown to undergo a facile and reversible C—C/C—B bond rearrangement upon irradiation with UV-light, quenching the emission of the sample and limiting their use in optoelectronic devices. It also disclosed Stoke's shift.

Article titled "Steric and electronic influence on photochromic switching of N,C-chelate four-coordinate organoboron compounds" by Hazem Amarne et al. published in Chemistry—A European Journal, 2010, 16(16):4750-61 reports a four-coordinate organoboron compound B(ppy) Mes(2) (1, ppy=2-phenylpyridyl, Mes=mesityl) was previously found to undergo reversible photochromic switching through the formation/breaking of a C—C bond, accompanied by a dramatic color change from colorless to dark blue.

Article titled "N^N- and N^C chelate four-coordinate organoboron compounds: synthesis, properties and applications" by Jiasheng Lu published as thesis 2013 reports the synthesis of N^N- and N^C-chelate four coordinate organoboron compounds and the investigation of their photophysical and photochemical properties.

US Pat. Appl. No. 20120253044 discloses organoboron compounds are described that upon exposure to light, absorb light and isomerize and form a dark-colored isomer. The dark-colored isomer converts back to the colorless isomer upon removal of light, or exposure to oxygen or heat. Such compounds can be added into polymeric matrices such as films.

Inspired by the prior art reports, the present inventors felt a need to provide novel class of N,C-chelate four-coordinate organoborons with different emission colors. The present inventors further observed that with the appropriate choice of the substituents on boron or quinoline, full color tunability can be obtained which can span the whole visible region.

Objective of the Invention

The main objective of the present invention is to provide novel class of N,C-chelate four-coordinate organoborons of Formula (I) with different emission colors useful in biology and in optoelectronic devices.

The another objective of the present invention is to achieve colourtunability both in solid and solution state through the substituent's on either quinolines or on boron centre of N,C-chelate four-coordinate organoborons of Formula (I).

Still another objective of the present invention is to provide molecular fluorophores based on N,C-Chelate four-coordinate organoborons which exhibit fluorescence with a large Stokes shift, range of quantum yield and exhibit solvatochromism.

SUMMARY OF THE INVENTION

Accordingly, the present invention provides N,C-Chelate four-coordinate organoborons of Formula (I), wherein said organoborons exhibit tunable emission colours that cover the whole visible region, useful in bio imaging and in optoelectronic devices

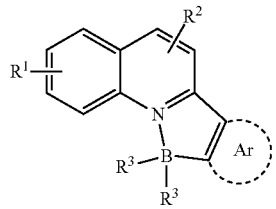

wherein,
$R^1$, $R^2$ and $R^3$ are selected independently from hydrogen, halogen, (un)substituted alkyl, (un)substituted aryl, (un) substituted heteroaryl, (un)substituted heterocylic group; more particularly, $R^1$, $R^2$ is H; $R^3$ is selected from methyl, ethyl, "Octyl, phenyl. 'ringAr' represent (un)substituted aryl, (un)substituted heteroaryl, (un)substituted heterocylic group, more particularly, Ar is selected from benzothiophenyl, pyrenyl, phenathrenyl, N,N-diphenyl aniline (Ph$_2$N—C$_6$H$_4$), Carbazole-C$_6$H$_4$, dimethyl aniline (Me$_2$N—C$_6$H$_4$).

In an embodiment, the present invention provides N,C-Chelate four-coordinate organoborons of Formula (I) that exhibit color tunability both in solid and solution state that In another embodiment, the present invention provides novel full-color tunable light emitter based on N,C-chelate four-coordinate organoborons having excellent Quantum yield, stokes shift and solvatochromism of Formula (I).

In still another embodiment, the present invention provides a process for synthesis of N,C-Chelate four-coordinate organoborons of Formula (I) comprising the steps of:
 a) reacting 2-amino benzaldehyde with suitable alkyne in presence of Au(I) as catalyst and an amine to obtain 2-substituted quinoline;
 b) reacting 2-substituted quinoline with boron tribromide (BBr$_3$) to get stable 2-(2-dibromoborylaryl) pyridines followed by further treating with trialkylaluminium (AlR$_3$) to obtain quinoline-borane complex of Formula (I).

In yet another embodiment, said metal catalyst is selected from Au(I), Chloro(triphenylphosphine)gold(I) (PPh$_3$AuCl) and silver triflate (AgOTf).

In still another embodiment, said suitable alkyne is selected from 2-ethynylbenzo[b]thiophene, 4-ethynyl-N,N-diphenylaniline, 1-ethynylpyrene, 9-(4-ethynylphenyl)-9H-carbazole, 9-ethynylphenanthrene, and 4-ethynyl-N,N-dimethylaniline.

In still another embodiment, said trialkylaluminium is selected from trimethylaluminium, triethylaluminium, trioctylaluminium, triphenylaluminium.

BRIEF DESCRIPTION OF THE DRAWINGS

FIG. 2: (a) depicts solvatochromism of compound 2a in UV spectra and (b) depict solvatochromism of compound 2a in fluorescence spectra.

DETAILED DESCRIPTION OF THE INVENTION

Figure 1B:
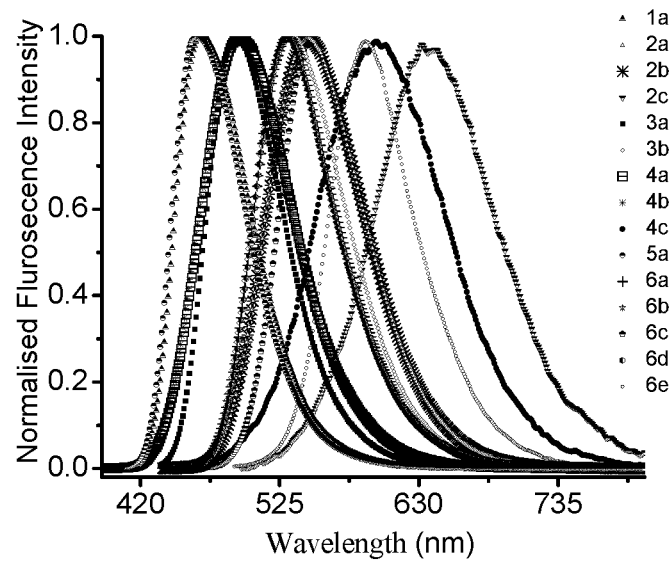
FIG. 1: (a) depicts fluorescence spectra of compound 1a-6e in DCM and (b) depict fluorescence spectra of compound 1a-6e as powder.
Figure 1B:
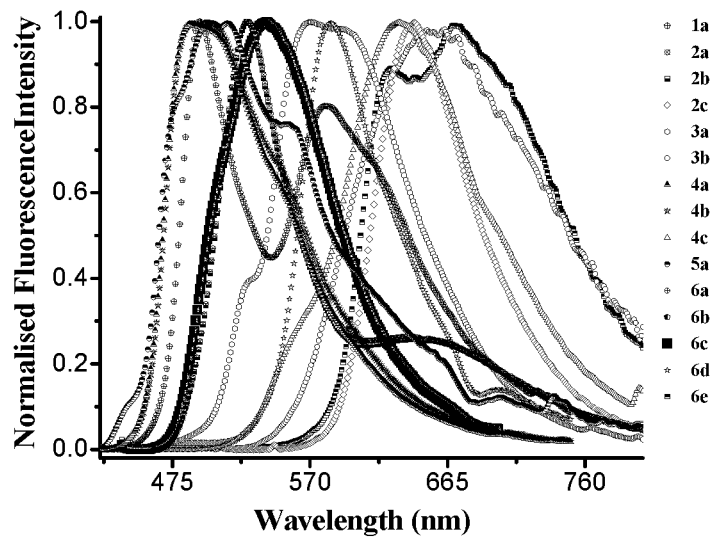

The invention will now be described in detail in connection with certain preferred and optional embodiments, so that various aspects thereof may be more fully understood and appreciated.

The present invention provides N,C-Chelate four-coordinate organoborons of Formula (I), wherein said organoborons exhibit tunable emission colours that cover the whole visible region, useful in bio imaging and in optoelectronic devices

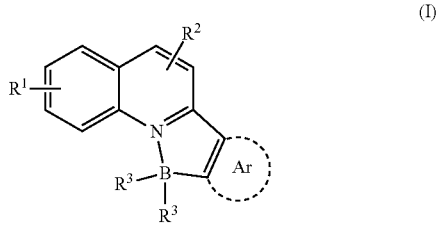

(I)

wherein,
$R^1$, $R^2$ and $R^3$ are selected independently from hydrogen, halogen, (un)substituted alkyl, (un)substituted aryl, (un)substituted heteroaryl, (un)substituted heterocylic group; more particularly, $R^1$, $R^2$ is H; $R^3$ is selected from methyl, ethyl, $^n$Octyl, phenyl.

'ringAr' represent (un)substituted aryl, (un)substituted heteroaryl, (un)substituted heterocylic group, more particularly, Ar is selected from benzothiophenyl, pyrenyl, phenathrenyl, $Ph_2N\text{—}C_6H_4$, Carbazole-$C_6H_4$, $Me_2N\text{—}C_6H_4$.

In an embodiment, the present invention provides N,C-Chelate four-coordinate organoborons of Formula (I) exhibit color tunability both in solid and solution state that can span the entire region of visible spectrum.

In another embodiment, the present invention provides novel full-color tunable light emitter based on N,C-chelate four-coordinate organoborons having excellent Quantum In an embodiment, the N,C-Chelate four-coordinate organoborons of Formula (I) and their spectral and physical data are given in Table 1 below:

| Compounds | Spectral and physical data |
|---|---|
| 1a<br>12,12-dimethyl-12H-12,14,13,14 benzo[4',5']thieno[3',2':3,4][1,2]azaborolo[1,5-a]quinoline | bluish solid, 91% yield; mp = 207-208° C.; $R_f$ = 0.55(Pet. ether/EtOAc = 80/20); $^1$H NMR (500 MHz, CDCl$_3$) δ = 8.56 (d, J = 8.5 Hz, 1 H), 8.33 (d, J = 8.5 Hz, 1 H), 8.18-8.11 (m, 1 H), 7.99-7.94 (m, 1 H), 7.92 (d, J = 8.2 Hz, 1 H), 7.88-7.82 (m, 1 H), 7.71 (d, J = 8.5 Hz, 1 H), 7.57 (t, J = 7.5 Hz, 1 H), 7.48-7.37 (m, 2 H), 0.43 (s, 6 H); $^{13}$C NMR (126 MHz, CDCl$_3$) δ = 154.5, 146.5, 142.5, 140.6, 140.5, 133.4, 131.6, 129.0, 126.5, 126.4, 126.0, 125.8, 124.5, 123.4, 122.3, 116.6, 8.9; HRMS (ESI) calcd for $C_{19}H_{17}NBS$ (M$^+$ + H) 302.1169, found 302.1169. |
| 2a<br>11,11-dimethyl-N,N-diphenyl-11H-11,14,12,14-benzo[3,4][1,2]azaborolo[1,5-a]quinolin-9-amine | greenish yellow solid, 90% yield; mp = 168-169° C.; $R_f$ = 0.60(Pet. ether/EtOAc = 80/20); $^1$H NMR (400 MHz, CDCl$_3$) δ = 8.66-8.56 (m, 1 H), 8.31 (d, J = 8.8 Hz, 1 H), 7.99-7.89 (m, 2 H), 7.87-7.78 (m, 2 H), 7.64-7.54 (m, 1 H), 7.45 (dd, J = 3.7, 5.9 Hz, 1 H), 7.42-7.33 (m, 4 H), 7.33-7.26 (m, 4 H), 7.21-7.12 (m, 2 H), 7.07-6.96 (m, 1 H), 0.32 (br. s., 6 H); $^{13}$C NMR (101 MHz, CDCl$_3$) δ = 157.2, 150.5, 147.6, 142.1, 139.8, 131.1, 129.4, 129.3, 128.7, 127.0, 125.7, 125.4, 125.3, 123.4, 123.3, 123.0, 121.4, 119.7, 115.5, 9.2; HRMS (ESI) calcd for $C_{29}H_{26}N_2B$ (M$^+$ + H) 413.2184, found 413.2179. |
| 2b<br>11,11-dioctyl-N,N-diphenyl-11H-11,14,12,14-benzo[3,4][1,2]azaborolo[1,5-a]quinolin-9-amine | yellow solid, 56% yield; mp = 155-156° C. $R_f$ = 0.70(Pet. ether/EtOAc = 90/10); $^1$H NMR (400 MHz, CDCl$_3$) δ = 8.52 (d, J = 8.8 Hz, 1 H), 8.30 (d, J = 8.6 Hz, 1 H), 7.90 (d, J = 8.1 Hz, 1 H), 7.93 (d, J = 8.6 Hz, 1 H), 7.81-7.76 (m, 2 H), 7.56 (d, J = 7.3 Hz, 1 H), 7.39 (s, 1 H), 7.29 (d, J = 7.6 Hz, 5 H), 7.22 (s, 4 H), 7.09 (d, J = 7.1 Hz, 2 H), 6.96 (d, J = 8.3 Hz, 1 H), 1.43 (br. s., 2 H), 1.35 (s, 2 H), 1.30 (br. s., 13 H), 1.04-0.79 (m, 10 H), 0.29 (t, J = 7.6 Hz, 6 H); $^{13}$C NMR (101 MHz, CDCl$_3$) δ = 158.3, 150.0, 147.7, 142.3, 139.7, 131.2, 129.4, 129.2, 128.7, 125.8, 125.1, 123.2, 123.0, 122.6, 122.4, 120.1, 115.3, 113.2, 31.9, 31.4, 30.2, 29.7, 29.4, 22.7, 17.1, 14.1, 14.1, 10.0; HRMS (ESI) calcd for $C_{43}H_{54}N_2B$ (M$^+$ + H) 609.4153, found 609.4155. |

| Compounds | Spectral and physical data |
|---|---|
| 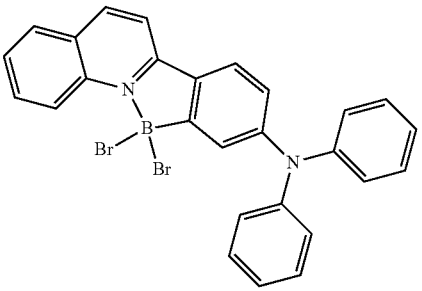<br>2c<br>11,11-dibromo-N,N-diphenyl-11H-11,14,12,14-benzo[3,4][1,2]azaborolo[1,5-a]quinolin-9-amine | red solid, 95% yield; mp = 289-290° C.; $R_f$ = 0.30(DCM/MeOH = 95/05); $^1$H NMR (400 MHz, CD$_2$Cl$_2$) δ-d$_2$ = 9.10-9.01 (m, 1 H), 8.50 (d, J = 8.8 Hz, 1 H), 7.98 (d, J = 7.3 Hz, 2 H), 7.86 (d, J = 8.6 Hz, 1 H), 7.71 (d, J = 8.6 Hz, 1 H), 7.68-7.60 (m, 1 H), 7.43-7.32 (m, 5 H), 7.26-7.17 (m, 6 H), 6.98 (dd, J = 2.4, 8.6 Hz, 1 H); $^{13}$CNMR (101 MHz, CD$_2$Cl$_2$) δ-d$_2$) □ = 147.1, 145.2, 132.9, 130.3, 129.7, 128.3, 127.7, 127.0, 126.3, 125.5, 124.9, 123.9, 121.2, 120.6, 115.8; HRMS (ESI) calcd for C$_{27}$H$_{20}$N$_2$BBr$_2$ (M$^+$ + H) 543.0060, found 543.0061. |
| 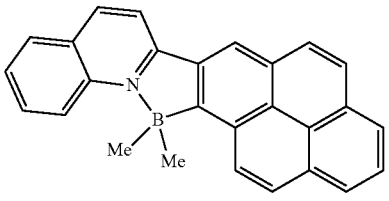<br>3a<br>14,14-dimethyl-14H-13,14,14,14-pyreno[1′,2′:3,4][1,2]azaborolo[1,5-a]quinolone | dark yellow solid, 86% yield; mp = 192-193° C.; $R_f$ = 0.62(Pet. ether/EtOAc = 80/20); $^1$H NMR (400 MHz, CDCl$_3$) δ = 9.03 (d, J = 9.3 Hz, 1 H), 8.94 (d, J = 9.0 Hz, 1 H), 8.83 (d, J = 9.3 Hz, 1 H), 8.55-8.46 (m, 2 H), 8.29 (d, J = 9.5 Hz, 1 H), 8.23 (dd, J = 5.9, 7.3 Hz, 2 H), 8.19-8.10 (m, 2 H), 8.05-7.97 (m, 2 H), 7.95-7.88 (m, 1 H), 7.69-7.60 (m, 1 H), 0.47 (s, 6 H); $^{13}$C NMR (101 MHz, CDCl$_3$) δ = 147.4, 140.2, 131.4, 129.9, 128.7, 128.7, 128.5, 128.3, 128.2, 127.0, 126.5, 126.0, 125.5, 125.4, 125.3, 123.8, 122.1, 119.8, 1.0; HRMS (ESI) calcd for C$_{27}$H$_{21}$N$_2$B (M$^+$ + H) 370.1785, found 370.1785. |
| 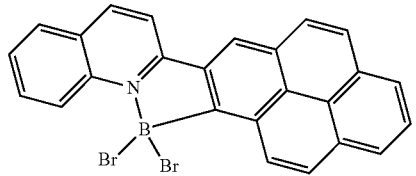<br>3b<br>14,14-dibromo-14H-13,14,14,14-pyreno[1′,2′:3,4][1,2]azaborolo[1,5-a]quinolone | reddish solid, 85% yield; mp = 155-156° C.; $R_f$ = 0.85 (Pet. ether/EtOAc = 90/10); 1H NMR (500 MHz, CDCl3) δ = 8.49-8.37 (m, 2 H), 8.31-8.24 (m, 2 H) 8.24-8.17 (m, 2 H), 7.98-7.93 (m, 1 H), 7.91-7.86 (m, 1 H), 7.84-7.73 (m, 3 H), 7.62-7.53 (m, 3 H), 7.52-7.45 (m, 2 H), 7.41-7.32 (m, 2 H); 13C NMR (126 MHz, CDCl3) δ = 156.3, 148.3, 140.6, 138.6, 138.5, 136.9, 129.8, 129.7, 129.3, 129.0, 127.5, 127.2, 126.4, 126.0, 123.5, 120.3, 120.1, 118.7, 113.1, 109.8; HRMS (ESI) calcd for C$_{25}$H$_{20}$O$_2$N$_2$F$_3$ (M$^+$ + H) 437.1471, found 437.1469. |
| 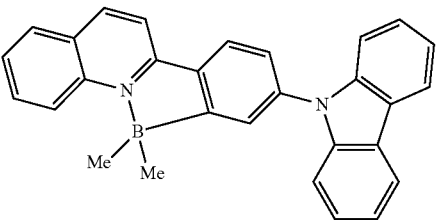<br>4a<br>9-(9H-carbazol-9-yl)-11,11-dimethyl-11H-11,14,12,14-benzo[3,4][1,2]azaborolo[1,5-a]quinoline | yellow solid, 88% yield; mp = 201-202° C.; $R_f$ = 0.56(Pet. ether/EtOAc = 80/20); $^1$H NMR (400 MHz, CDCl$_3$) δ = 8.70 (d, J = 8.8 Hz, 1 H), 8.44 (d, J = 8.6 Hz, 1H) 8.17 (d, J = 8.1 Hz, 1 H), 8.20 (d, J = 7.6 Hz, 2 H), 8.12 (d, J = 8.8 Hz, 1 H), 8.01-7.95 (m, 2 H), 7.90 (ddd, J = 1.6, 7.0, 8.7 Hz, 1 H), 7.69-7.62 (m, 3 H), 7.56 (dd, J = 2.0, 8.1 Hz, 1 H), 7.51-7.43 (m, 2 H), 7.37-7.30 (m, 2 H), 0.39 (s, 6 H); $^{13}$C NMR (101 MHz, CDCl$_3$) δ□ = 156.9, 142.1, 140.7, 140.6, 139.9, 134.1, 131.5, 128.9, 127.6, 126.5, 125.9, 123.6, 123.6, 123.5, 123.4, 120.2, 120.0, 115.7, 110.3, 9.1; HRMS (ESI) calcd for C$_{29}$H$_{24}$N$_2$B (M$^+$ + H) 411.2027, found 411.2028 |

-continued

| Compounds | Spectral and physical data |
|---|---|
| 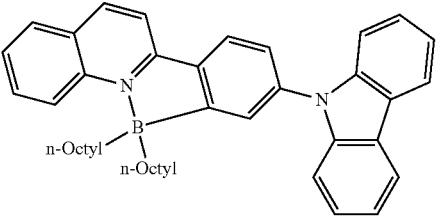<br>4b<br>9-(9H-carbazol-9-yl)-11,11-dioctyl-11H-11,14,12,14-benzo[3,4][1,2]azaborolo[1,5-a]quinoline | yellow solid, 55% yield; mp = 188-189° C. $R_f$ = 0.72(Pet. ether/EtOAc = 90/10); $^1$H NMR (400 MHz, CDCl$_3$) δ = 8.68 (d, J = 8.8 Hz, 1 H), 8.45 (d, J = 8.8 Hz, 1 H), 8.21 (d, J = 7.8 Hz, 3 H), 8.14 (d, J = 8.8 Hz, 1 H), 7.99 (d, J = 8.1 Hz, 1 H), 7.96-7.93 (m, 1 H), 7.90 (d, J = 8.3 Hz, 1 H), 7.68-7.64 (m, 1 H), 7.62 (d, J = 8.1 Hz, 2 H), 7.58-7.55 (m, 1 H), 7.49 (d, J = 7.1 Hz, 2 H), 7.34 (t, J = 7.3 Hz, 2 H), 1.37 (br. s., 2 H), 1.29 (s, 11 H), 1.24 (br. s., 1 H), 1.16 (dd, J = 7.7, 13.8 Hz, 4 H), 1.03 (dd, J = 7.5, 13.8 Hz, 4 H), 0.96-0.79 (m, 6 H), 0.40 (t, J = 7.6 Hz, 6 H); $^{13}$C NMR (101 MHz, CDCl$_3$) δ = 157.9, 142.3, 140.8, 140.5, 139.4, 137.1, 135.5, 131.6, 129.9, 129.7, 129.1, 128.9, 127.5, 127.4, 127.3, 127.0, 126.6, 126.0, 125.9, 123.6, 123.4, 122.8, 120.4, 120.3, 120.1, 119.9, 118.8, 115.5, 110.2, 109.9, 31.9, 29.7, 29.4, 22.7, 17.1, 17.0, 14.1, 10.1; HRMS (ESI) calcd for C$_{43}$H$_{52}$N$_2$B (M$^+$ + H) 607.4153, found 607.4155. |
| 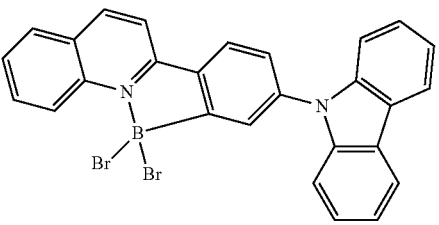<br>4c<br>11,11-dibromo-9-(9H-carbazol-9-yl)-11H-11,14,12,14-benzo[3,4][1,2]azaborolo[1,5-a]quinolone | orange solid, 88% yield; mp = 231-232° C.; $R_f$ = 0.40(DCM/MeOH = 95/05); $^1$H NMR (400 MHz, CDCl$_3$) δ = 8.45-8.39 (m, 2 H) 8.32 (d, J = 8.6 Hz, 1H) 8.24 (d, J = 8.6 Hz, 1 H), 8.18 (d, J = 7.8 Hz, 2 H), 7.99 (d, J = 8.6 Hz, 1 H), 7.90 (dd, J = 1.5, 8.3 Hz, 1 H), 7.81-7.75 (m, 3 H), 7.61-7.56 (m, 1 H), 7.53 (d, J = 8.1 Hz, 2 H), 7.47-7.44 (m, 2 H), 7.34 (d, J = 6.8 Hz, 2 H), 7.23-7.19 (m, 1 H), 6.77 (t, J = 7.5 Hz, 1 H), 6.68-6.64 (m, 1 H); $^{13}$C NMR (101 MHz, CDCl$_3$) δ = 137.1, 129.9, 129.7, 129.4, 129.1, 127.5, 127.3, 126.5, 126.2, 126.0, 123.5, 120.3, 120.1, 118.9, 113.3, 109.8; HRMS (ESI) calcd for C$_{27}$H$_{18}$N$_2$BBr$^{81}$Br (M$^+$ + H) 540.9904, found 540.9903. |
| 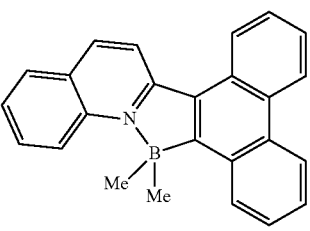<br>5a<br>9,9-dimethyl-9H-9,14,10,14-phenanthro[9′,10′:3,4][1,2]azaborolo[1,5-a]quinoline | bluish green solid, 85% yield; mp = 242-243° C.; $R_f$ = 0.80(Pet. ether/EtOAc = 90/10); $^1$H NMR (500 MHz, CDCl$_3$) δ = 8.86 (td, J = 0.8, 8.2 Hz, 1H) 8.81- 8.77 (m, 2 H), 8.77-8.74 (m, 1 H), 8.72 (d, J = 8.9 Hz, 1 H), 8.64 (dd, J = 2.0, 7.5 Hz, 1 H), 8.41 (d, J = 8.9 Hz, 1 H), 7.96-7.92 (m, 1 H), 7.88 (ddd, J = 1.7, 6.9, 8.8 Hz, 1 H), 7.79-7.69 (m, 3 H), 7.68-7.64 (m, 1 H), 7.60 (t, J = 7.5 Hz, 1 H), 0.59 (s, 6 H); $^{13}$C NMR (126 MHz, CDCl$_3$) δ = 158.4, 142.0, 140.0, 131.2, 131.1, 128.8, 128.2, 126.9, 126.7, 126.6, 126.5, 125.0, 124.0, 123.3, 123.2, 123.0, 122.6, 119.1, 10.9; HRMS (ESI) calcd for C$_{25}$H$_{21}$NB (M$^+$ + H) 346.1762, found 346.1762. |
| 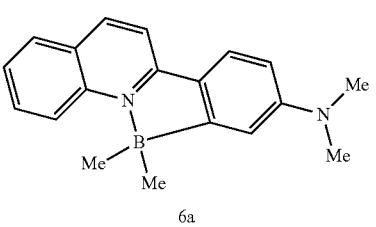<br>6a<br>N,N,11,11-tetramethyl-11H-11,14,12,14-benzo[3,4][1,2]azaborolo[1,5-a]quinolin-9-amine | yellow solid, 88% yield; mp = 154-156° C.; $R_f$ = 0.62(Pet. ether/EtOAc = 80/20); $^1$H NMR (400 MHz, CDCl$_3$) δ = 8.54 (d, J = 8.6 Hz, 1 H), 8.17 (d, J = 8.8 Hz, 1 H), 7.89-7.80 (m, 3 H), 7.80-7.72 (m, 1 H), 7.48 (t, J = 7.6 Hz, 1 H), 7.05-6.94 (m, 1 H), 6.73-6.65 (m, 1 H), 3.14 (s, 6 H), 0.41-0.21 (m, 6 H); $^{13}$C NMR (101 MHz, CDCl$_3$) δ = 157.8, 152.4, 142.2, 139.3, 130.8, 128.7, 126.6, 124.9, 124.5, 123.9, 122.5, 115.4, 110.4, 109.9, 40.4, 9.54; HRMS (ESI) calcd for C$_{19}$H$_{22}$N$_2$B (M$^+$ + H) 289.1871, found 289.1871. |

-continued

| Compounds | Spectral and physical data |
|---|---|
| 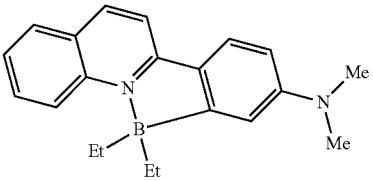<br>6b<br>11,11-diethyl-N,N-dimethyl-11H-11,14,12,14-benzo[3,4][1,2]azaborolo[1,5-a]quinolin-9-amine | yellow solid, 88% yield; mp = 154-156° C.; $R_f$ = 0.70(Pet. ether/EtOAc = 90/10); $^1$H NMR (400 MHz, CDCl$_3$) δ = 8.47 (d, J = 8.8 Hz, 1 H), 8.20 (d, J = 8.8 Hz, 1 H), 7.93-7.79 (m, 3 H), 7.74 (ddd, J = 1.6, 7.0, 8.7 Hz, 1 H), 7.55-7.43 (m, 1 H), 6.95 (d, J = 2.7 Hz, 1 H), 6.69 (dd, J = 2.4, 8.6 Hz, 1 H), 3.13 (s, 6 H), 1.02-0.86 (m, 4H), 0.40-0.26 (m, 6 H); $^{13}$C NMR (101 MHz, CDCl$_3$) δ = 159.0, 152.1, 142.5, 139.2, 130.9, 128.6, 126.3, 126.2, 125.0, 123.5, 122.0, 115.2, 111.0, 109.7, 40.4, 9.9; HRMS (ESI) calcd for $C_{21}H_{26}N_2B$ (M$^+$ + H) 317.2184, found 317.2182. |
| 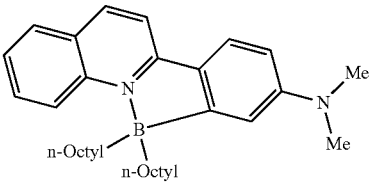<br>6c<br>N,N-dimethyl-11,11-dioctyl-11H-11,14,12,14-benzo[3,4][1,2]azaborolo[1,5-a]quinolin-9-amine | yellow solid, 55% yield; mp = 176-177° C. $R_f$ = 0.75(Pet. ether/EtOAc = 90/10); $^1$H NMR (400 MHz, CDCl$_3$) δ = 8.48 (d, J = 8.8 Hz, 1 H), 8.20 (d, J = 8.8 Hz, 1 H), 7.88-7.79 (m, 3 H), 7.78-7.70 (m, 1 H), 7.48 (t, J = 7.5 Hz, 1 H), 6.96 (dd, J = 0.5, 2.2 Hz, 1 H), 6.69 (dd, J = 2.4, 8.6 Hz, 1 H), 3.14 (s, 6 H), 1.34-1.21 (m, 14 H), 1.07-0.77 (m, 14 H), 0.33 (t, J = 7.7 Hz, 6 H); $^{13}$C NMR (101 MHz, CDCl$_3$) δ = 158.9, 152.0, 142.4, 139.2, 130.9, 128.6, 126.3, 126.2, 125.0, 123.5, 122.0, 115.2, 111.0, 109.7, 40.4, 31.9, 29.7, 29.6, 29.4, 22.7, 14.1, 9.9; HRMS (ESI) calcd for $C_{33}H_{50}N_2B$ (M$^+$ + H) 485.4095, found 485.4097. |
| 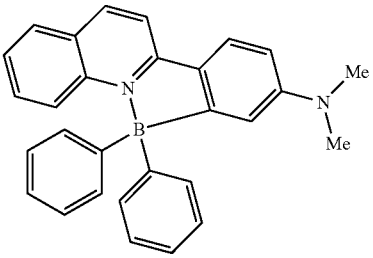<br>6d<br>N,N-dimethyl-11,11-diphenyl-11H-11,14,12,14-benzo[3,4][1,2]azaborolo[1,5-a]quinolin-9-amine | orange solid, 46% yield; mp = 289-290° C.; $R_f$ = 0.62(Pet. ether/EtOAc = 80/20); $^1$H NMR (400 MHz, CDCl$_3$) δ = 8.31 (d, J = 8.6 Hz, 1 H), 8.00-7.94 (m, 2 H), 7.85-7.77 (m, 2 H), 7.55 (d, J = 8.6 Hz, 1 H), 7.34 (td, J = 1.2, 7.5 Hz, 5 H), 7.19-7.14 (m, 4 H), 7.12-7.08 (m, 2 H), 6.91 (d, J = 2.4 Hz, 1 H), 6.62 (s, 1 H), 3.01 (s, 6 H); $^{13}$C NMR (126 MHz, CDCl$_3$) δ = 160.2, 153.1, 142.0, 140.7, 139.3, 133.5, 131.1, 128.4, 127.1, 126.6, 125.3, 125.0, 124.5, 124.0, 123.7, 119.1, 115.4, 114.1, 111.7, 110.2, 40.3; HRMS (ESI) calcd for $C_{29}H_{26}N_2B$ (M$^+$ + H) 413.2117, found 413.2114. |
| 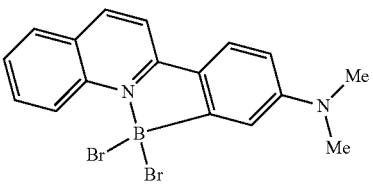<br>6e<br>11,11-dibromo-N,N-dimethyl-11H-11,14,12,14-benzo[3,4][1,2]azaborolo[1,5-a]quinolin-9-amine | red solid, 91% yield; mp = 168-169° C.; $R_f$ = 0.32(DCM/MeOH = 95/05); $^1$H NMR (500 MHz, CD$_2$Cl$_2$) δ-d$_2$) = 8.16-8.10 (m, 3 H), 7.86 (d, J = 8.5 Hz, 1 H), 7.80 (d, J = 7.6 Hz, 1 H), 7.69 (t, J = 7.2 Hz, 1 H), 7.51-7.42 (m, 1 H), 6.83 (d, J = 7.9 Hz, 2 H), 3.05 (br. s., 6 H); $^{13}$C NMR (126 MHz, CD$_2$Cl$_2$) δ-d$_2$) = 157.3, 152.2, 148.2, 144.4, 137.2, 132.5, 130.2, 129.1, 129.0, 128.0, 127.2, 126.0, 118.6, 112.5, 112.2, 40.6; HRMS (ESI) calcd for $C_{17}H_{16}N_2BBr^{81}Br$ (M$^+$ + H) 418.9747, found 418.9745. |

In still another embodiment, the present invention provides a process for synthesis of N,C-Chelate four-coordinate organoborons of Formula (I) comprising the steps of:
a) reacting 2-amino benzaldehyde with suitable alkyne in presence of metal as catalyst and an amine to obtain 2-substituted quinoline;
b) reacting 2-substituted quinoline with boron tribromide (BBr$_3$) to get stable 2-(2-dibromoborylaryl) pyridines followed by further treating with trialkylaluminium (AlR$_3$) to obtain quinoline-borane complex of Formula (I).

In yet another embodiment, said metal catalyst is selected from Au(I), Chloro(triphenylphosphine)gold(I) (PPh$_3$AuCl), silver triflate (AgOTf).

In still another embodiment, said suitable alkyne is selected from 2-ethynylbenzo[b]thiophene, 4-ethynyl-N,N-diphenylaniline, 1-ethynylpyrene, 9-(4-ethynylphenyl)-9H-carbazole, 9-ethynylphenanthrene, 4-ethynyl-N,N-dimethylaniline.

In still another embodiment, said trialkylaluminium is selected from trimethylaluminium, triethylaluminium, trioctylaluminium, triphenylaluminium.

In further embodiment, the present invention provides a novel full-color tunable light emitter based on N,C-chelate four-coordinate organoborons having excellent Quantum yield, stokes shift, fluorescent life time and solvate chromism of Formula (I)

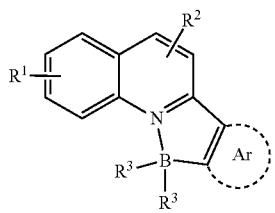

(I)

wherein,
$R^1$, $R^2$ and $R^3$ are selected independently from hydrogen, halogen, (un)substituted alkyl, (un)substituted aryl, (un)substituted heteroaryl, (un)substituted heterocylic group; said $R^1$, $R^2$ is selected from hydrogen, $R^3$ is selected from Methyl, Ethyl, $^n$Octyl, Phenyl;
'ringAr' represent (un)substituted aryl, (un)substituted heteroaryl, (un)substituted heterocylic group; said Ar is selected from Benzothiophenyl, Pyrenyl, Phenathrenyl, $Ph_2N—C_6H_4$, Carbazole-$C_6H_4$, $Me_2N—C_6H_4$;
said Quantum yield is ranging from 0.9 to 0.81;
said stokes shift is in solid state ranging from 93 to 197 and in solution state ranging from 60 to 165; and
said fluorescent lifetime is ranging from 2.1 to 6.9.

The process is as shown in Scheme 1 below:

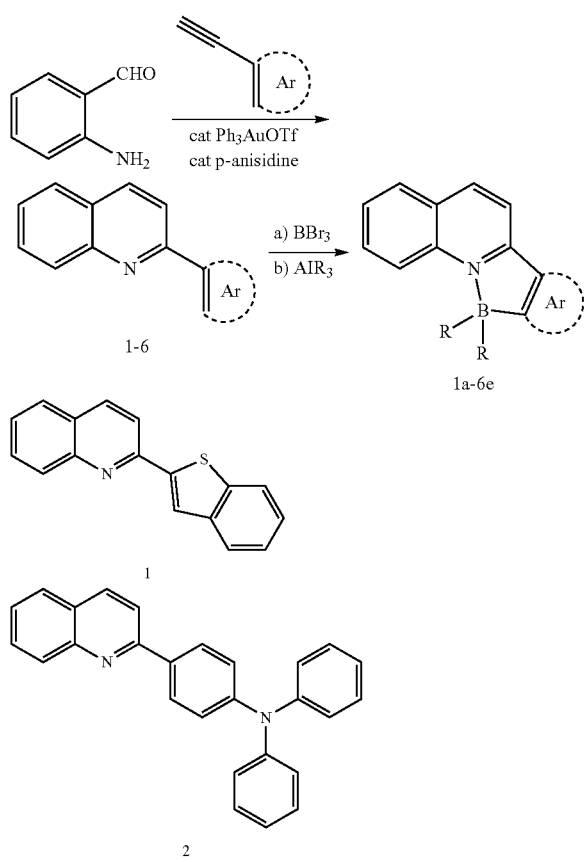

Scheme 1

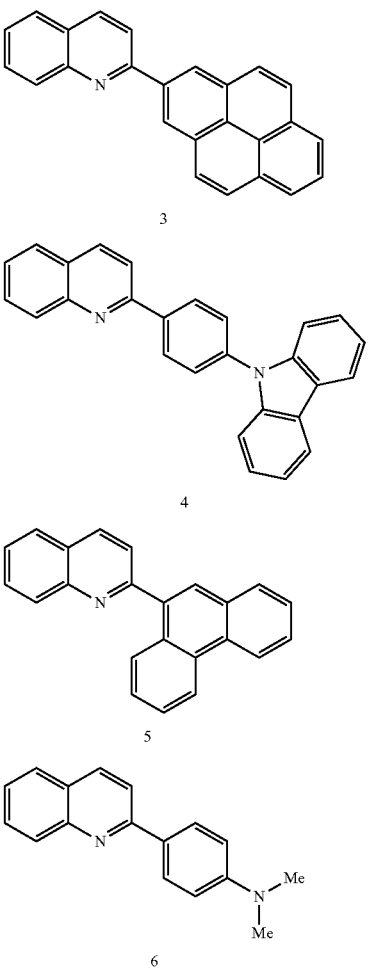

1a: Ar = Benzothiophenyl, R = Me
2a: Ar = p-Ph$_2$NC$_6$H$_3$, R = Me
2b: Ar = p-Ph$_2$NC$_6$H$_3$, R = n-Octyl
2c: Ar = p-Ph$_2$NC$_6$H$_3$, R = Br
3a: Ar = Pyrenyl, R = Me
3b: Ar = Pyrenyl, R = Br
4a: Ar = p-CarbazolylC$_6$H$_3$, R = Me
4b: Ar = p-CarbazolylC$_6$H$_3$, R = n-Octyl
4c: Ar = p-CarbazolylC$_6$H$_3$, R = Br
5a: Ar = Phenanthryl, R = Me
6a: Ar = p-Me$_2$NC$_6$H$_3$, R = Me
6b: Ar = p-Me$_2$NC$_6$H$_3$, R = Et
6c: Ar = p-Me$_2$NC$_6$H$_3$, R = n-Octyl
6d: Ar = p-Me$_2$NC$_6$H$_3$, R = Phenyl
6e: Ar = p-Me$_2$NC$_6$H$_3$, R = Br The terminal alkynes used in the process are prepared according to known procedure and comprises the following:

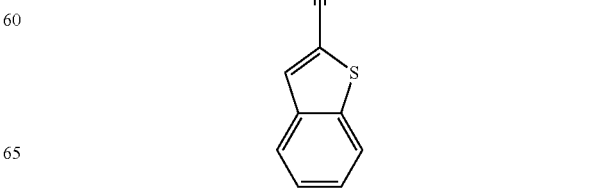

a

-continued

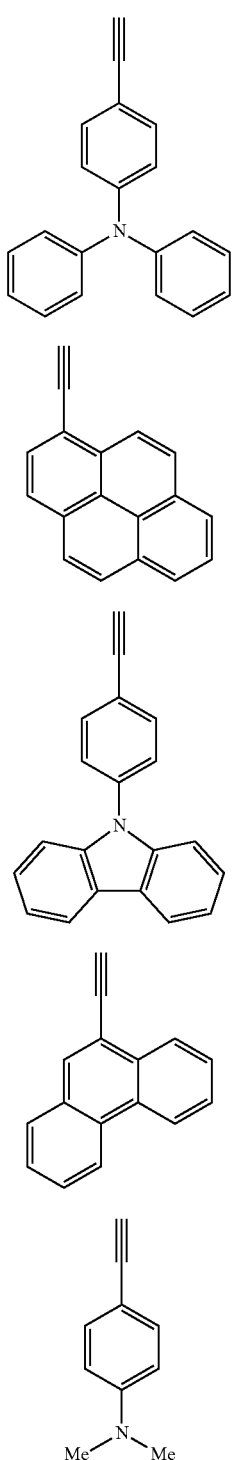

B. Blanco, A. Sedes, A. Peón, H. Lamb, A. R. Hawkins, L. Castedoc, C. González-Bello, *Org. Biomol. Chem.*, 2012, 10, 3662; M. Planells, A. Abate, D. J. Hollman, S. D. Stranks, V. Bharti, J. Gaur, D. Mohanty, S. Chand, H. J. Snaith, N. Robertson, *J. Mater. Chem. A*, 2013, 1, 6949; V. V. Filichev, I. V. Astakhova, A. D. Malakhov, V. A. Korshun, E. B. Pedersen, *Chem. Eur. J.*, 2008, 14, 9968; M. Hayashi, R. Sakamoto, H. Nishihara, *Chem. Eur. J.*, 2012, 18, 8610; S. Grunder, D. M. Torres, C. Marquardt, A. Blaszczyk, R. Krupke, M. Mayor, *Eur. Org. Chem.*, 2011, 478-496; R. C. Lirag, Ha T. M. Le, O. Š. Miljanić, *Chem. Commun.*, 2013, 49, 4304.

The 2-substituted quinolines (1-6) prepared by step (a) comprises:

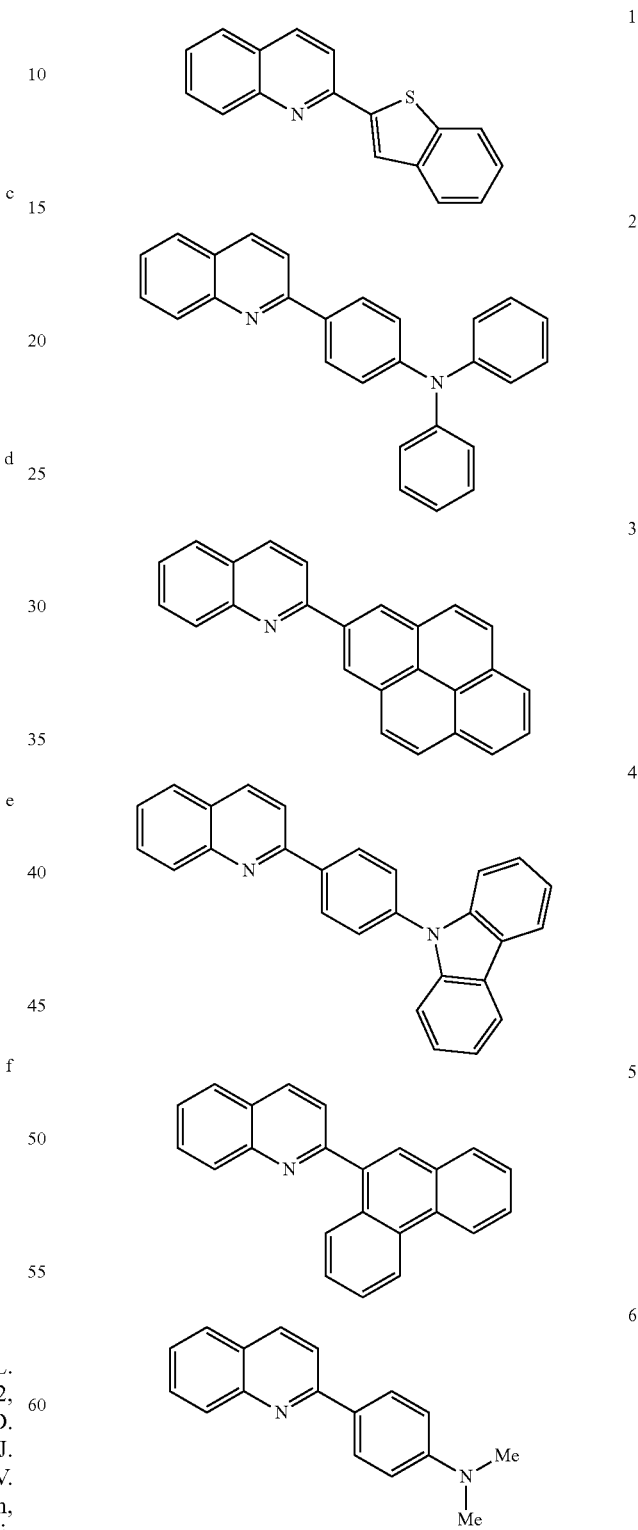

The intermediate 2-(2-dibromoborylaryl) pyridines are stable enough to be handled in air and serve as the synthetic platform for variously substituted pyridine-borane complexes. The N,C-chelate four-coordinate organoborons derivatives (Formula I) produced are stable in air and water, have high thermal stability as indicated by TGA.

In preferred embodiment, the compounds of general Formula (I) (i.e. 1a to 6e) show intense fluorescence both in solution and solid state. The compounds exhibited broad absorption band between 387-491 nm with regards to the electronic transition originating from the π-molecular orbitals. The fluorescence spectra of complexes 1a-6e in both solution and the solid state were recorded and shown in FIGS. 1a and 1b. The fluorophores exhibited intense emission in $CH_2Cl_2$ solutions when excited at their absorption maxima. The emission profiles of these compounds in solution, having emission bands that peaked at 466 nm (1a) to 637 nm (2c), covering a wide range from blue to red, reflected that the substituent at the 2nd position of quinoline was effective in tuning the emission color of this type of N,C-chelate four-coordinate organoborons.

Further, the solid-state fluorescence spectra of the compounds in powder forms are measured and are shown in FIGS. 1a and 1b. The fluorescence of the solid samples with emission peaks at 491 nm (for 1a) and 670 nm (for 6e) also covered a wide range from blue to deep red. The emission maxima of complexes 1a-6a in solid state shows blue and red shifts compared with those of solution state which reflected crystallochromy effects. This indicates that all the solid samples are highly emissive with excellent quantum yields. The absolute fluorescence quantum yields of solutions were calculated using an integrating sphere method. The methyl group substituted on boron atom compounds showed good quantum yield ($\phi_f$ 0.81 for 3a) compared to bromo substituent ($\phi_f$ 0.03 for 2c).

The photophysical data for compounds 1a-6e including Stokes shift, quantum yields, and fluorescence lifetime are given in Table 2 below:

TABLE 2

Photophysical data for compounds 1a-6e

| Compound | Δ Stokes (nm)[a] | | $\phi_f$[b] | $\tau_f$ |
|---|---|---|---|---|
| | solution | solid | $CH_2Cl_2$ | (ns)[f] |
| 1a | 060 | 098 | 0.58 | 5.2 |
| 2a | 113 | 118 | 0.56 | 6.4 |
| 2b | 114 | 115 | 0.60 | 6.0 |
| 2c | 146 | 165 | 0.03 | 2.1 |
| 3a | 073 | 194 | 0.81 | 4.0 |
| 3b | 080 | 188 | 0.60 | 4.8 |
| 4a | 110 | 093 | 0.71 | 6.2 |
| 4b | 105 | 097 | 0.67 | 6.1 |
| 4c | 165 | 197 | 0.09 | 3.2 |
| 5a | 058 | 106 | 0.78 | 5.5 |
| 6a | 098 | 149 | 0.50 | 6.6 |
| 6b | 099 | 142 | 0.59 | 6.2 |
| 6c | 101 | 133 | 0.58 | 6.9 |
| 6d | 097 | 117 | 0.43 | 6.9 |
| 6e | 102 | 180 | 0.14 | 2.5 |

[c]Stokes shift = λem − λabs;
[e]Quantum yields;
[f]fluorescent lifetime

In another embodiment, the compounds N,C-chelate four-coordinate organoborons also showed positive solvatochromic behaviour as emission wavelengths are found to be red shifted with increase in solvent polarity (FIG. 2).

The electrochemical properties of N,C-chelate four-coordinate organoborons (Formula I) were investigated by cyclic voltammetry (CV). All luminogens exhibited similar CV curves with two irreversible oxidation peaks. The low LUMO value of N,C-chelate four-coordinate organoborons was comparable to those of silole derivatives (e.g., −2.77 and −2.81 eV), indicating that BNC (boron, nitrogen and carbon) is a potential electron transporter. The electrochemical properties are given in Table 3.

TABLE 3

Electrochemical properties of compounds of 1a to 6e:

| Sr. No | Compound | $\lambda_{exc\ (nm)}$[a] | $E_{onset}$ | HOMO (ev)[b] | LUMO (ev)[c] | Δ (ev)[d] |
|---|---|---|---|---|---|---|
| 1 | 1a | 433 | 1.03 | −5.43 | −2.57 | 2.86 |
| 2 | 2a | 480 | 0.58 | −4.98 | −2.40 | 2.58 |
| 3 | 2c | 544 | 0.65 | −5.05 | −2.78 | 2.27 |
| 4 | 3a | 453 | 1.19 | −5.59 | −2.86 | 2.73 |
| 5 | 3b | 496 | 1.13 | −5.53 | −3.03 | 2.50 |
| 6 | 4a | 431 | 0.93 | −5.33 | −2.46 | 2.87 |
| 7 | 4c | 495 | 1.06 | −5.46 | −2.96 | 2.50 |
| 8 | 5a | 431 | 1.02 | −5.42 | −2.55 | 2.87 |
| 9 | 6a | 483 | 0.47 | −4.87 | −2.31 | 2.56 |
| 10 | 6e | 540 | 1.01 | −5.41 | −3.12 | 2.29 |

[a]wavelength estimated from the onset of absorption spectrum;
[b]HOMO = −(4.4 + $E_{onset}$)
[c]LUMO = −(HOMO + Eg);
[d]the energy gap between the HOMO and LUMO In yet another embodiment, the present invention relates to the use of N,C-chelate four-coordinate organoborons for in vitro bio-imaging and in optoelectronic devices.

The following examples, which include preferred embodiments, will serve to illustrate the practice of this invention, it being understood that the particulars shown are by way of example and for purpose of illustrative discussion of preferred embodiments of the invention.

Example 1: General Procedure Preparation of Alkynes

The terminal alkynes a, b, c, d, e and f are prepared according to literature known procedure.

a) Synthesis of Trimethyl(Phenylethynyl)Silane Derivatives:

To a solution of Aryl bromide/iodide derivatives (25 mmol), CuI (1.0 mmol, 190 mg) and $Pd(PPh_3)_2Cl_2$ (0.5 mmol, 350 mg) in dried THF (25 ml) was added triethylamine (50 mmol, 5.0 g). A solution of trimethylsilylacetylene (37.5 mmol, in 5.0 ml of THF) was then added dropwise via syringe under nitrogen. The resulting solution was stirred at room temperature for 12 h. The reaction mixture was filtered through Celite and the solvent was removed by rotary evaporation. The residue was treated with water and extracted with ethyl ether. The combined organic layer was washed with brine and dried over magnesium sulfate. After the removal of solvent, the crude product was purified with silica gel column chromatography (ethyl acetate/petroleum ether, v/v=1/100) affording pure trimethyl(phenyl ethynyl) silane derivatives).

2) Synthesis of Aryl Acetylene Derivatives Via Desilylation Reactions:

To a solution of trimethyl(phenylethynyl)silane derivatives (10 mmol) in methanol (20 ml) and $CH_2Cl_2$ (10 ml) (v/v=2:1) was added $K_2CO_3$ (30 mmol, 4.2 g) and stirred at RT for 12 h. The resulting mixture was treated with water and extracted with ethyl ether. The combined organic layer was washed with brine and dried over magnesium sulfate. The solvent was removed and the residue was distilled carefully under reduced pressure or purified by silica gel column chromatography to afford the pure products.

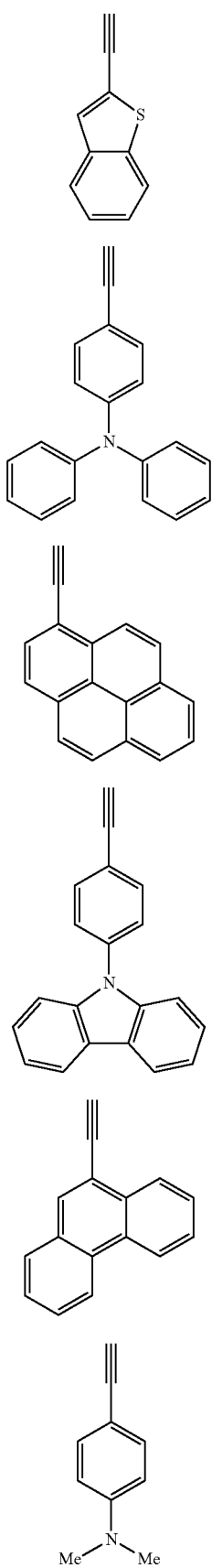

Example 2: General Procedure for Preparation of Various 2 Substituted Quinolines (1-6)

To a screw-cap vial containing stir bar, were added 2-amino-benzaldehydes (0.3 mmol), terminal alkynes (0.36 mmol, 1.2 equiv.), PPh$_3$AuCl (2 mol %), AgOTf (2 mol %), dry DCE (2 ml) and p-anisidine (25 mol %). The reaction vial was fitted with cap, evacuated and filled with nitrogen and heated at 100° C. for 12 h. The reaction mixture was allowed to bring to ambient temperature. The reaction mixture was diluted with ethyl acetate and filtered through a plug of silica gel. The filtrate was concentrated under reduced pressure and the resulting residue was purified by column chromatography (silica gel, hexane/EtOAc) to give the desired 2 substituted quinolines.

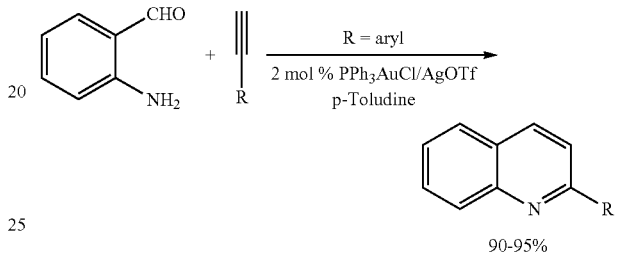

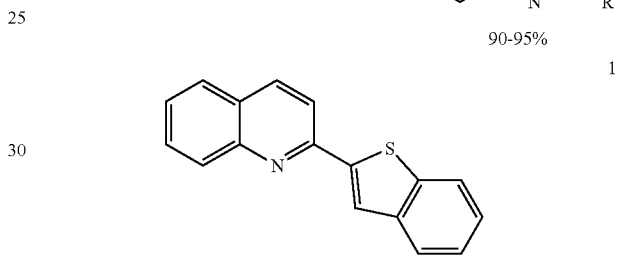

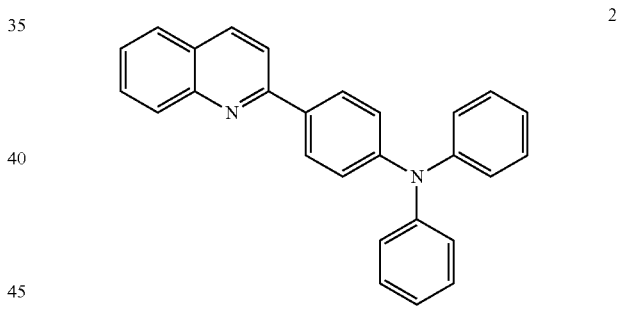

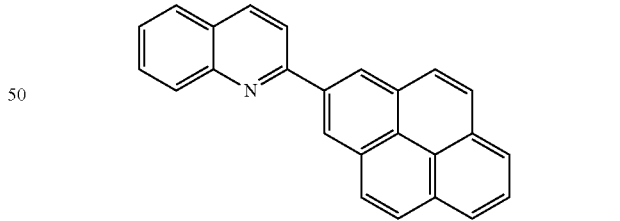

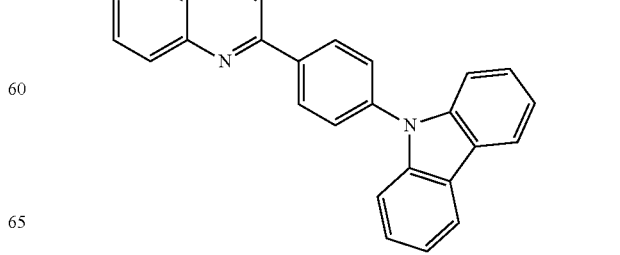

-continued

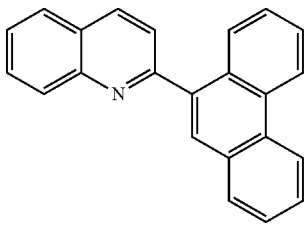

5

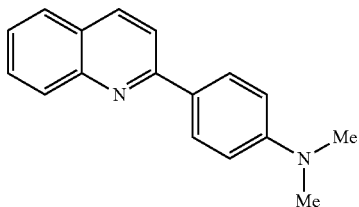

6

TABLE 4

The compounds 1-6 and their physical and spectral data are as follows:

| compounds | Physical and spectral data |
| --- | --- |
| 1 | light yellow solid, 88% yield; mp = 198-199° C.; $R_f$ = 0.90(Pet. ether/EtOAc = 90/10); $^1$H NMR (400 MHz, CDCl$_3$) δ = 8.21-8.14 (m, 2 H), 8.00-7.97 (m, 1 H), 7.96-7.90 (m, 2 H), 7.88-7.83 (m, 1 H), 7.82-7.78 (m, 1 H), 7.74 (ddd, J = 1.5, 6.8, 8.6 Hz, 1 H), 7.57-7.50 (m, 1 H), 7.43-7.36 (m, 2 H); $^{13}$C NMR (101 MHz, CDCl$_3$) δ = 152.2, 148.0, 145.4, 141.1, 140.4, 136.6, 129.9, 129.4, 127.5, 126.5, 125.3, 124.5, 124.3, 122.6, 122.4, 117.8, 113.2; HRMS (ESI) calcd for C$_{17}$H$_{12}$NS (M$^+$ + H) 262.0685, found 262.0683. |
| 2 | light yellow solid, 92% yield: mp = 162-163° C.; $R_f$ = 0.75(Pet. ether/EtOAc = 90/10); $^1$H NMR (400 MHz, CDCl$_3$) δ = 8.22-8.13 (m, 2 H), 8.11-8.02 (m, 2 H), 7.87-7.77 (m, 2 H), 7.76-7.69 (m, 1 H), 7.55-7.46 (m, 1 H), 7.36-7.28 (m, 4 H), 7.26-7.16 (m, 6 H), 7.13-7.05 (m, 2 H); $^{13}$C NMR (101 MHz, CDCl$_3$) δ = 156.9, 149.0, 148.3, 147.4, 136.6, 133.2, 129.5, 129.3, 128.4, 127.4, 126.9, 125.9, 124.8, 123.3, 123.1, 118.6; HRMS (ESI) calcd for C$_{27}$H$_{21}$N$_2$ (M$^+$ + H) 373.1699, found 373.1698. |
| 3 | light yellow solid, 88% yield: mp = 148-149° C.; $R_f$ = 0.82(Pet. ether/EtOAc = 90/10); $^1$H NMR (400 MHz, CDCl$_3$) δ = 8.46 (d, J = 9.3 Hz, 1 H), 8.36 (d, J = 8.6 Hz, 1 H), 8.34-8.27 (m, 3 H), 8.26-8.19 (m, 2 H), 8.15 (s, 2 H), 8.10 (d, J = 9.3 Hz, 1 H), 8.08-8.01 (m, 1 H), 8.00-7.93 (m, 1 H), 7.88 (d, J = 8.3 Hz, 1 H), 7.83 (ddd, J = 1.5, 6.9, 8.5 Hz, 1 H), 7.68-7.61 (m, 1 H); $^{13}$C NMR (101 MHz, CDCl$_3$) δ = 159.7, 148.3, 136.2, 135.9, 131.6, 131.4, 130.9, 129.8, 129.8, 128.8, 128.2, 128.0, 127.7, 127.6, 127.4, 126.9, 126.6, 126.0, 125.4, 125.1, 124.9, 124.8, 123.8; HRMS (ESI) calcd for C$_{25}$H$_{16}$N (M$^+$ + H) 330.1277, found 330.1277. |
| 4 | light yellow solid, 82% yield; mp = 155-156° C.; $R_f$ = 0.85(Pet. ether/EtOAc = 90/10); $^1$H NMR (500 MHz, CDCl$_3$) δ = 8.49-8.37 (m, 2 H), 8.31-8.24 (m, 2 H), 7.98-7.93 (m, 1 H), 7.91-7.86 (m, 1 H), 7.84-7.73 (m, 3 H), 7.62-7.53 (m, 3 H), 7.52-7.45 (m, 2 H), 7.41-7.32 (m, 2 H); $^{13}$C NMR (126 MHz, CDCl$_3$) δ = 156.3, 148.3, 140.6, 138.6, 138.5, 136.9, 129.8, 129.7, 129.3, 129.0, 127.5, 127.2, 126.4, 126.0, 123.5, 120.3, 120.1, 118.7, 113.1, 109.8; HRMS (ESI) calcd for C$_{27}$H$_{19}$N$_2$ (M$^+$ + H) 371.1543, found 371.1541. |

TABLE 4-continued

The compounds 1-6 and their physical and spectral data are as follows:

| compounds | Physical and spectral data |
|---|---|
| 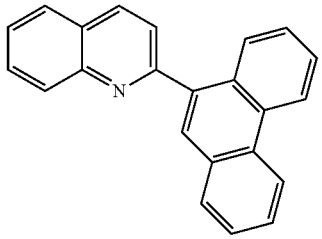<br>5 | off white solid, 90% yield; mp = 118-119° C. $R_f$ = 0.88(Pet. ether/EtOAc = 90/10); $^1$H NMR (500 MHz, CDCl$_3$) δ = 8.82 (d, J = 8.2 Hz, 1 H), 8.77 (d, J = 8.2 Hz, 1 H), 8.32 (d, J = 8.2 Hz, 1 H), 8.28 (d, J = 8.5 Hz, 1 H), 8.15-8.09 (m, 1 H), 8.00 (s, 1 H), 7.99-7.97 (m, 1 H), 7.96-7.93 (m, 1 H), 7.82 (ddd, J = 1.7, 6.9, 8.5 Hz, 1 H), 7.77 (d, J = 8.2 Hz, 1 H), 7.75-7.68 (m, 2 H), 7.67-7.61 (m, 2 H), 7.58 (ddd, J = 1.4, 6.9, 8.2 Hz, 1 H); $^{13}$C NMR (126 MHz, CDCl$_3$) δ = 159.4, 148.1, 137.4, 136.3, 136.2, 131.3, 130.8, 130.5, 130.3, 129.8, 129.7, 129.1, 128.8, 128.5, 128.3, 127.6, 127.1, 126.8, 126.8, 126.7, 126.6, 126.1, 123.4, 123.3, 123.0, 122.6; HRMS (ESI) calcd for C$_{23}$H$_{16}$N (M$^+$ + H) 306.1277, found 306.1278. |
| 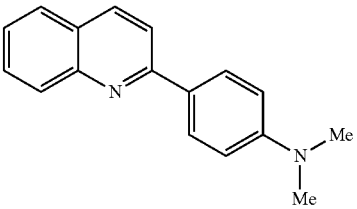<br>6 | off white solid, 86% yield; mp = 180-181° C. $R_f$ = 0.82(Pet. ether/EtOAc = 90/10); $^1$H NMR (400 MHz, CDCl$_3$) δ = 8.17-8.07 (m, 4 H), 7.84 (d, J = 8.6 Hz, 1 H), 7.80-7.75 (m, 1 H), 7.72-7.65 (m, 1 H), 7.49-7.41 (m, 1 H), 6.88-6.81 (m, 2 H), 3.06 (s, 6 H); $^{13}$C NMR (101 MHz, CDCl$_3$) δ = 157.3, 151.3, 148.4, 136.2, 129.3, 128.4, 127.3, 126.7, 125.3, 118.3, 112.2, 40.3; HRMS (ESI) calcd for C$_{17}$H$_{17}$N$_2$ (M$^+$ + H) 249.1386, found 249.1386. |

Example 3: General Procedure for Electrophilic Aromatic Borylation of 2-Substituted Quinolines To a stirred solution of 2-substituted quinolines (200 mg, 0.65 mmol) and i-Pr$_2$NEt (86 mg, 0.65 mmol) in CH$_2$Cl$_2$ (0.5 mL) at 0° C. was added BBr$_3$ (1.0M in CH$_2$Cl$_2$ 2.0 mL, 1.9 mmol). After being stirred at room temperature for 24 h, saturated K$_2$CO$_3$ aqueous solution was added to the reaction mixture. The reaction was poured into water, the organic layer was separated and extracted with CH$_2$Cl$_2$ (twice), washed with water (once), brine (once), dried over Na$_2$SO$_4$ and concentrated. The resulting solid was collected by filtration and washed with hexane to give quinoline-borane complex (280 mg, 89% yield).

Example 4: General Procedure for Bromine-Alkyl Group Exchange with Trialkyl-Aluminium To a stirred solution of quinoline-borane complex (200 mg, 0.35 mmol) in toluene/CH$_2$Cl$_2$ (1:1) at room temperature was added Me$_3$Al (1.1 M in hexane, 0.75 mL, 0.77 mmol). After being stirred at this temperature for 5 min, the reaction was quenched by adding water. The organic layer was separated and extracted with CH$_2$Cl$_2$ (twice), washed with water (once), brine (once), and dried over MgSO$_4$ and concentrated. After filtration and solvent evaporation, the residue was purified by silica-gel column chromatography by using hexane/EtOAc mixture as eluent. A pale yellow solid was obtained in 91% yield to afford product.

The compounds 1a to 6e prepared by the above process was characterized by UV-vis absorption and fluorescence spectra both in solution (DCM) and in solid state (FIGS. 1a and 1b).

Example 5: Calculation of Quantum Yields

The absolute fluorescence quantum yields of solutions were calculated using an integrating sphere method. The methyl group substituted on boron atom compounds showed good quantum yield ($\phi_f$ 0.81 for 3a) compare to bromo substituent ($\phi_f$ 0.03 for 2c).

Example 6: Measurement of Fluorescence Lifetime

The Fluorescence lifetime for all organoboranes 1a-6e were measured in CH$_2$Cl$_2$ upon excitation at 431 nm and 591 nm. Data were taken at 431, 591 and emission peak of each compound. All compounds showed more or less similar lifetime values ranging in between 2.5-6.9 ns.

The photophysical data for compounds 1a-6e including Stokes shift, quantum yields, and fluorescence lifetime are given in Table 5 below:

| Compound | Δ Stokes (nm)$^a$ | | $\phi_f^b$ | $\tau_f$ |
|---|---|---|---|---|
| | solution | solid | CH$_2$Cl$_2$ | (ns)$^f$ |
| 1a | 060 | 098 | 0.58 | 5.2 |
| 2a | 113 | 118 | 0.56 | 6.4 |
| 2b | 114 | 115 | 0.60 | 6.0 |
| 2c | 146 | 165 | 0.03 | 2.1 |
| 3a | 073 | 194 | 0.81 | 4.0 |
| 3b | 080 | 188 | 0.60 | 4.8 |
| 4a | 110 | 093 | 0.71 | 6.2 |
| 4b | 105 | 097 | 0.67 | 6.1 |
| 4c | 165 | 197 | 0.09 | 3.2 |
| 5a | 058 | 106 | 0.78 | 5.5 |
| 6a | 098 | 149 | 0.50 | 6.6 |
| 6b | 099 | 142 | 0.59 | 6.2 |
| 6c | 101 | 133 | 0.58 | 6.9 |
| 6d | 097 | 117 | 0.43 | 6.9 |
| 6e | 102 | 180 | 0.14 | 2.5 |

$^a$Stokes shift = λem − λabs;
$^b$Quantum yields;
$^f$fluorescent lifetime

Example 7: Cyclic Voltametry

The electrochemical properties of N,C-chelate four-coordinate organoborons were investigated by cyclic voltammetry (CV). All luminogens exhibited similar CV curves with two irreversible oxidation peaks. The oxidation onset potentials (Eonset) of N,C-chelate four-coordinate organoborons occur between 0.47 to 1.19 V, from which the HOMO energy levels were determined to be −4.87 to −5.59 eV (HOMO=−(4.4+Eonset)). Their LUMO energy levels can be obtained from the optical band gap energies (Eg) and the HOMO values (LUMO=−(HOMO+Eg), and are located between −2.77 to −2.81 eV. The low LUMO value of N,C-chelate four-coordinate organoborons is comparable to those of silole derivatives (e.g., −2.77 and −2.81 eV), indicating that BNC is a potential electron transporter.

TABLE 6

Electrochemical properties of compounds of 1a to 6e:

| Sr. No | Compound | $\lambda_{exc\,(nm)}$ [a] | $E_{onset}$ | HOMO (ev) [b] | LUMO (ev) [c] | Δ (ev) [d] |
|---|---|---|---|---|---|---|
| 1 | 1a | 433 | 1.03 | −5.43 | −2.57 | 2.86 |
| 2 | 2a | 480 | 0.58 | −4.98 | −2.40 | 2.58 |
| 3 | 2c | 544 | 0.65 | −5.05 | −2.78 | 2.27 |
| 4 | 3a | 453 | 1.19 | −5.59 | −2.86 | 2.73 |
| 5 | 3b | 496 | 1.13 | −5.53 | −3.03 | 2.50 |
| 6 | 4a | 431 | 0.93 | −5.33 | −2.46 | 2.87 |
| 7 | 4c | 495 | 1.06 | −5.46 | −2.96 | 2.50 |
| 8 | 5a | 431 | 1.02 | −5.42 | −2.55 | 2.87 |
| 9 | 6a | 483 | 0.47 | −4.87 | −2.31 | 2.56 |
| 10 | 6e | 540 | 1.01 | −5.41 | −3.12 | 2.29 |

[a] wavelength estimated from the onset of absorption spectrum;
[b] HOMO = −(4.4 + $E_{onset}$)
[c] LUMO= −(HOMO + Eg);
[d] the energy gap between the HOMO and LUMO Example 8: X-ray Crystallography Data X-ray intensity data measurements of compounds 2a, 3a, 4a, 5a, and 6b were carried out on a Bruker SMART APEX II CCD diffractometer with graphite-monochromatized (MoK$_\alpha$=0.71073 Å) radiation. The X-ray generator was operated at 50 kV and 30 mA. A preliminary set of cell constants and an orientation matrix were calculated from three sets of 36 frames. Data were collected with ωscan width of 0.5° at different settings of φ and 2θ with a frame time of 10 sec for 2a, 3a, 6b and 15, 20 sec for 4a, 5a respectively, keeping the sample-to-detector distance fixed at 5.00 cm. The X-ray data collection was monitored by APEX2 program (Bruker, 2006). All the data were corrected for Lorentzian, polarization and absorption effects using SAINT and SADABS programs (Bruker, 2006). SHELX-97 was used for structure solution and full matrix least-squares refinement on F$^2$. All the hydrogen atoms were placed in geometrically idealized positionand constrained to ride on their parent atoms. An ORTEP view of all five compounds were drawn with 50% probability displacement ellipsoids and H atoms are shown as small spheres of arbitrary radii.

TABLE 7

Crystal data table

| | 2a | 3a | 4a | 5a | 6b |
|---|---|---|---|---|---|
| Mol. Formula | $C_{29}H_{25}BN_2$ | $C_{27}H_{20}BN$ | $C_{29}H_{23}BN_2$ | $C_{25}H_{20}BN$ | $C_{21}H_{25}BN_2$ |
| Mr | 412.32 | 369.25 | 410.30 | 345.23 | 316.24 |
| Temp. (K) | 200(2) | 293(2) | 293(2) | 150(2) | 150(2) |
| Crystal System | monoclinic | monoclinic | triclinic | monoclinic | triclinic |
| Space group | P2$_1$/n | P2$_1$/c | P¯1 | P2$_1$/n | P¯1 |
| a/Å | 17.3899(3) | 8.8980(4) | 9.3145(5) | 13.9351(7) | 7.9636(2) |
| b/Å | 10.3122(2) | 7.0675(3) | 9.7778(6) | 9.0239(5) | 8.8054(2) |
| c/Å | 26.5129(5) | 30.3620(14) | 12.5665(7) | 14.1194(8) | 14.8492(5) |
| α/° | 90 | 90 | 83.550(3) | 90 | 106.476(2) |
| β/° | 108.4870(10) | 98.000(3) | 84.896(3) | 92.128(3) | 90.570(2) |
| γ/° | 90 | 90 | 76.744(3) | 90 | 116.512(2) |
| V/Å$^3$ | 4509.15(14) | 1890.78(15) | 1104.59(11) | 1774.28(17) | 882.12(4) |
| Z, D$_{calc}$/g cm$^{-3}$ | 8, 1.215 | 4, 1.297 | 2, 1.234 | 4, 1.292 | 2, 1.191 |
| μ/mm$^{-1}$ | 0.070 | 0.074 | 0.071 | 0.074 | 0.069 |
| F (000) | 1744 | 776 | 432 | 728 | 340 |
| θ max/° | 25.00 | 25.00 | 25.00 | 25.00 | 25.00 |
| Absor. correction | multi-scan | multi-scan | multi-scan | multi-scan | multi-scan |
| Refln. collected | 63086 | 13377 | 15850 | 22665 | 12311 |
| Unique refln. | 7928 | 3338 | 3879 | 3108 | 3115 |
| Observed refln. | 6507 | 2420 | 3046 | 2911 | 2747 |
| R$_{int}$ | 0.0588 | 0.0472 | 0.0305 | 0.0478 | 0.0213 |
| No. of Parameter | 581 | 265 | 291 | 247 | 221 |
| R$_1$_obs, R$_1$_all | 0.0776, 0.0965 | 0.0576, 0.0804 | 0.0586, 0.0755 | 0.1623, 0.1655 | 0.0417, 0.0481 |
| wR$_2$_obs, wR$_2$_all | 0.1548, 0.1640 | 0.1232, 0.1344 | 0.1330, 0.1416 | 0.4284, 0.4295 | 0.1004, 0.1044 |
| GoF | 1.150 | 1.068 | 1.114 | 1.212 | 1.027 |
| Δρ$_{max}$, Δρ$_{min}$/eÅ$^{-3}$ | 0.246, −0.255 | 0.187, −0.198 | 0.317, −0.200 | 0.588, −0.596 | 0.238, −0.188 |

Advantages of Invention:
Novel N,C-Chelate four-coordinate organoborons of formula (I), wherein said organoborons exhibit tunable solid-state emission colours that cover the whole visible region.
The compounds exhibit tunable emission both in solution and solid state.
Compounds are thermally stable, good quantum yields; high stokes shift and show positive solvatochromic behaviour.

We claim:

1. Novel N,C-chelate four-coordinate organoboron compounds of formula (I):

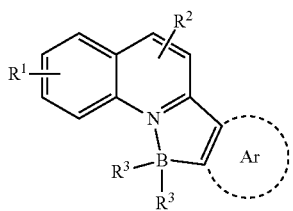

(I)

having excellent quantum yield, stokes shift, fluorescent lifetime and solvate chromism, as full color tunable light emitter,
wherein:
$R^1$ and $R^2$ are hydrogen;
$R^3$ is selected from the group consisting of Methyl, Ethyl, "Octyl, and Phenyl;
Ar is selected from the group consisting of Benzothiophenyl, Pyrenyl, Phenanthrenyl, $Ph_2N-C_6H_4$, Carbazole-$C_6H_4$, and $Me_2N-C_6H_4$;
said Quantum yield is ranging from 0.9 to 0.81;
said stokes shift is in solid state ranging from 93 to 197 nm and in solution state ranging from 60 to 165 nm;
said fluorescent lifetime is ranging from 2.1 to 6.9 ns;
wherein said compounds of formula (I) emit light in solid and solution states.

2. The compounds as claimed in claim 1, wherein the light emission of said compounds in visible spectrum is tunable.

3. The optoelectronic devices comprising compounds as claimed in claim 1.

4. A process for synthesis of N,C-Chelate four-coordinate organoboron compounds of formula (I) as claimed in claim 1 comprising the steps of:
a) reacting 2-amino benzaldehyde with suitable alkyne in presence of metal as catalyst and an amine to obtain 2-substituted quinoline, wherein:
said suitable alkyne is selected from the group consisting of 2-ethynylbenzo[b]thiophene, 4-ethynyl-N,N-diphenylaniline, 1-ethynylpyrene, 9-(4-ethynylphenyl)-9H-carbazole, 9-ethynylphenanthrene, and 4-ethynyl-N,N-dimethylaniline;
said metal catalyst is selected from the group consisting of Au(I), $PPh_3AuCl$, and AgOTf;
said amine is selected from the group consisting of p-toluidine and p-anisidine; and
b) reacting 2-substituted quinoline of step (a) with $BBr_3$ in presence of trialkylaluminium ($AlR_3$) to obtain N,C-chelate four-coordinate organoboron compounds of formula (I).

5. The process as claimed in claim 4, wherein said trialkylaluminium of step (b) is selected from the group consisting of trimethylaluminium, triethylaluminium, trioctylaluminium, and triphenylaluminium.

6. The compounds as claimed in claim 1, wherein the said compounds are selected from the group consisting of:
12,12-dimethyl-12H-12,14,13,14benzo[4',5']thieno[3',2':3,4][1,2]azaborolo[1,5-a]quinoline;
11,11-dimethyl-N,N-diphenyl-11H-11,14,12,14-benzo[3,4][1,2]azaborolo[1,5-a]quinolin-9-amine;
11,11-dioctyl-N,N-diphenyl-11H-11,14,12,14-benzo[3,4][1,2]azaborolo[1,5-a]quinolin-9-amine;
11,11-dibromo-N,N-diphenyl-11H-11,14,12,14-benzo[3,4][1,2]azaborolo[1,5-a]quinolin-9-amine;
14,14-dimethyl-14H-13,14,14,14-pyreno[1',2':3,4][1,2]azaborolo[1,5-a]quinoline;
14,14-dibromo-14H-13,14,14,14-pyreno[1',2':3,4][1,2]azaborolo[1,5-a]quinoline;
9-(9H-carbazol-9-yl)-11,11-dimethyl-11H-11,14,12,14-benzo[3,4][1,2]azaborolo[1,5-a]quinoline;
9-(9H-carbazol-9-yl)-11,11-dioctyl-11H-11,14,12,14-benzo[3,4][1,2]azaborolo[1,5-a]quinoline;
11,11-dibromo-9-(9H-carbazol-9-yl)-11H-11,14,12,14-benzo[3,4][1,2]azaborolo[1,5-a]quinoline;
9,9-dimethyl-9H-9,14,10,14-phenanthro[9',10':3,4][1,2]azaborolo[1,5-a]quinoline;
N,N,11,11-tetramethyl-11H-11,14,12,14-benzo[3,4][1,2]azaborolo[1,5-a]quinolin-9-amine;
11,11-diethyl-N,N-dimethyl-11H-11,14,12,14-benzo[3,4][1,2]azaborolo[1,5-a]quinolin-9-amine;
N,N-dimethyl-11,11-dioctyl-11H-11,14,12,14-benzo[3,4][1,2]azaborolo[1,5-a]quinolin-9-amine;
N,N-dimethyl-11,11-diphenyl-11H-11,14,12,14-benzo[3,4][1,2]azaborolo[1,5-a]quinolin-9-amine; and
11,11-dibromo-N,N-dimethyl-11H-11,14,12,14-benzo[3,4][1,2]azaborolo[1,5-a]quinolin-9-amine.

* * * * *